United States Patent [19]

Trell

[11] Patent Number: 4,669,486

[45] Date of Patent: Jun. 2, 1987

[54] DEVICE FOR TAKING AND DISPENSING BLOOD SAMPLES FOR THE PURPOSE OF DETERMINING BLOOD SEDIMENTATION

[76] Inventor: Anders Trell, Torkel Knutssonsgatan 35, S-116 51 Stockholm, Sweden

[21] Appl. No.: 775,051

[22] PCT Filed: Jan. 15, 1985

[86] PCT No.: PCT/SE85/00014

§ 371 Date: Aug. 23, 1985

§ 102(e) Date: Aug. 23, 1985

[87] PCT Pub. No.: WO85/03350

PCT Pub. Date: Aug. 1, 1985

[30] Foreign Application Priority Data

Jan. 20, 1984 [SE] Sweden ............................... 8400288

[51] Int. Cl.⁴ ............................................. A61B 5/14
[52] U.S. Cl. .................................... 128/764; 128/771; 604/203
[58] Field of Search ......................... 128/760, 762-766, 128/771; 604/264, 266, 181, 187, 200-203

[56] References Cited

U.S. PATENT DOCUMENTS

| | | | |
|---|---|---|---|
| 3,623,475 | 11/1971 | Sanz et al. | 128/762 |
| 3,734,079 | 5/1973 | Weber | 128/765 X |
| 3,910,103 | 10/1975 | Rose | 128/765 X |
| 3,978,846 | 9/1976 | Bailey | 128/762 |
| 4,392,497 | 7/1983 | Ghaussy | 128/764 X |
| 4,393,882 | 7/1983 | White | 128/764 |
| 4,434,802 | 3/1984 | Rilliet | 128/764 |
| 4,509,534 | 4/1985 | Tassin, Jr. | 128/764 |

FOREIGN PATENT DOCUMENTS

| | | | |
|---|---|---|---|
| 3025800 | 2/1982 | Fed. Rep. of Germany | 128/765 |
| 1410990 | 5/1966 | France | 128/763 |

Primary Examiner—Edward M. Coven
Assistant Examiner—Angela D. Sykes
Attorney, Agent, or Firm—Browdy and Neimark

[57] ABSTRACT

A device for taking and dispensing blood samples for the purpose of determining blood sedimentation, comprising a sampling tube (6) which is sealed against the ingress of air and liquid by means of a rubber stopper (8) and in which a partial vacuum either prevails or can be created by means of a displaceable plunger (14) arranged in the sampling tube. The sampling tube contains a given quantity of an anti-coagulant (9), and connected to the sampling tube (6), preferably integral therewith, is a pipette tube (7) having an inner diameter and a length conforming to the standards prescribed for the sedimentation reaction. According to one embodiment, the pipette tube (7) is sealed against the ingress of air and liquid and encloses a partial vacuum. One connection (10,11) between the interior of the sampling tube (6) and the interior of the pipette tube (7) is normally closed, but can be selectively opened, preferably by rotating the rubber stopper (8), so that a sample can be transferred from the interior of the sampling tube (6) to the interior of the pipette tube (7) under the influence of a partial vacuum in the pipette tube. Simultaneously herewith there is opened a connection (12,13) between the interior of the sampling tube (6) and the surrounding atmosphere, this connection suitably being normally closed. In an alternative embodiment, the pipette tube (7) is open at one end thereof and the sample is transferred from the sampling tube to the pipette tube through the connection therebetween, under the influence of an overpressure generated in the sampling tube with the aid of a plunger arranged for axial movement therein.

17 Claims, 4 Drawing Figures

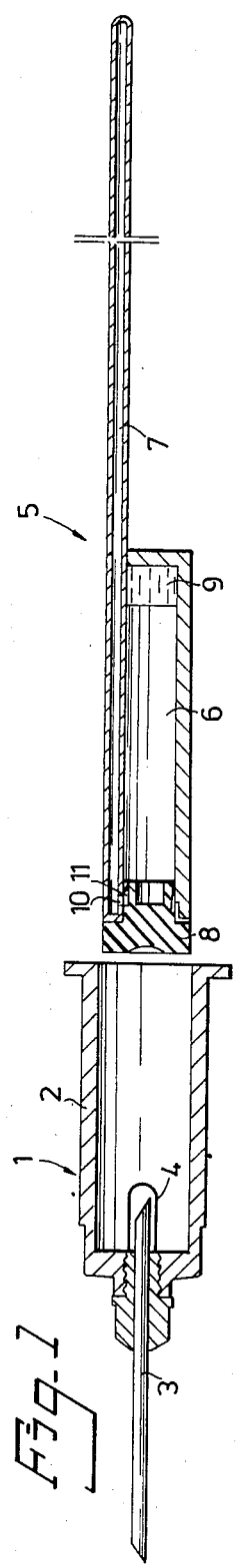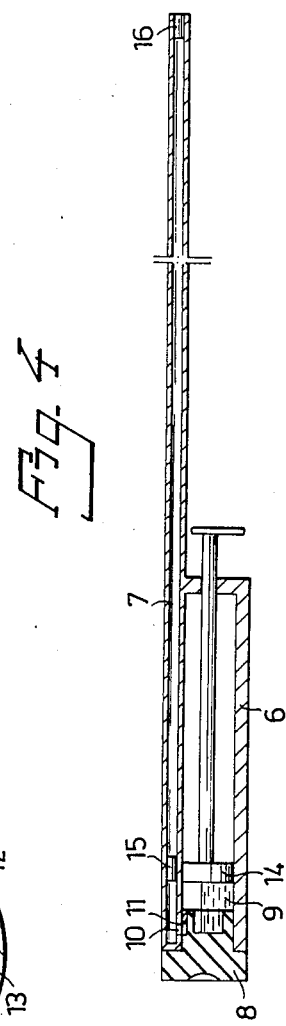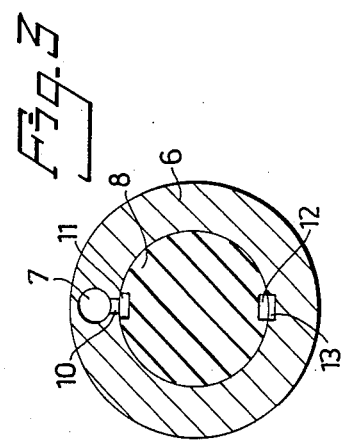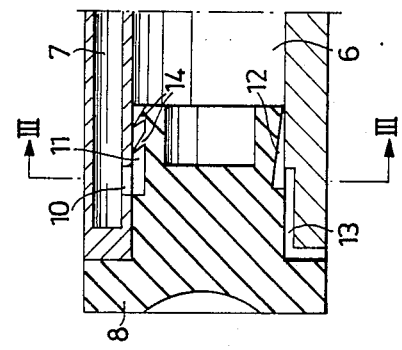

DEVICE FOR TAKING AND DISPENSING BLOOD SAMPLES FOR THE PURPOSE OF DETERMINING BLOOD SEDIMENTATION

TECHNICAL FIELD

The present invention relates to a device for taking and dispensing blood samples for the purpose of determining sedimentation of the blood.

BACKGROUND ART

Determination of blood sedimentation is a routine procedure which has been widely applied for many years. In principle, blood sedimentation values are determined by taking a blood sample from a patient and mixing the blood with an anti-coagulant, normally a sodium citrate solution. The sample is then dispensed into a straight, vertically arranged pipette tube of standard internal diameter, in Sweden normally 2.5 mm, so as to obtain in the tube a column of blood of standard height, in Sweden normally 200 mm. The tube is then allowed to stand at a standardised temperature for a standardised length of time, during which the so-called sedimentation reaction takes place, during which reaction the red blood corpuscles form so-called coin rolls and settle to the lower part of the blood column, while the plasma collects above the sedimented blood corpuscles. When the aforesaid standardised time period has lapsed, the height of the plasma column is read-off and the reading obtained used as a measurement of the rate at which the blood settles, i.e. the so-called blood sedimentation rate.

Since the test used to determine the sedimentation of blood is a standard test widely used, methods and devices are sought for which enable blood samples to be taken and dispensed as quickly and as simply as possible. At present the actual sampling of the blood is normally effected in an extremely rational fashion, with the aid of a so-called vacuum blood sampling tube, (for example of the Venoject ® or Vacutainer ® kind). The open end of one such vacuum sample tube is closed by means of a rubber stopper and the interior of the tube is held under a partial vacuum and contains a given amount of an anti-coagulent, normally a sodium citrate solution. Such a vacuum sampling tube is used together with a sampling holder, which has the appearance of a plungerless injection syringe having inserted into its forward end a throughpassing, double-pointed disposable needle or cannula. The externally located point of the needle or cannula is inserted into the vein of a patient and the vacuum sampling tube then inserted into the cylindrical cavity of the holder, so that the rubber stopper located in said one end of the tube is pierced by the internal pointed end of the needle. Because of the partial vacuum prevailing in the vacuum sampling tube, blood will be drawn through the needle or cannula into the sampling tube. When sufficient blood has been drawn into the sampling tube, the tube is withdrawn from the holder, whereupon the hole formed in the rubber stopper when piercing the same is automatically sealed-off by the rubber as a result of its intrinsic elasticity. The needle of the sampling holder can be left in the patient's vein and further blood samples taken in a similar manner. The vacuum sampling tube containing the blood sample is shaken from side to side a number of times, either manually or in a special cradle designed for this purpose, so as to mix the blood with the anti-coagulent to the extent desired. This is a simple and quick method of taking blood samples and also eliminates practically completely all risks of blood, which may be contaminated, from being spilled or allowed to run free during the process.

Other kinds of sampling tubes are also available (for example tubes retailed under the trade name Monovette ®). The only major difference between these tubes and those aforedescribed is that no partial vacuum is created within the tubes during their manufacture, but are instead provided with a manually displaceable plunger with which a partial vacuum can be created in the tube and blood drawn thereinto. In other respects the tubes function in the same manner as those beforedescribed.

In order to effect subsequent settling of the blood sample, it is necessary to dispense the mixture of blood and anti-coagulent from the sampling tube in which it is held to the aforesaid standardised pipette tube. In the methods normally applied hitherto (for example Sedipipette ®, Sedivac ®, and Sediplus ®) it is necessary to remove the rubber stopper from the vacuum sampling tube and to dispense part of the blood sampled to the pipette tube in some manner, until a blood column of prescribed height is obtained therein. This is a relatively complicated labour-consuming and time-consuming task which requires particular expertise and familiarity on the part of personnel performing the task. Consequently, it is normal practice for private medical clinics and small medical centres to send blood samples to larger laboratories for analysis, instead of determining the sedimentation themselves. This practice, however, has serious disadvantages, since the waiting period between the time at which the blood sample is taken and the time at which the blood is dispensed has an indefinible effect on the sedimentation reaction and therewith on the measuring result itself. The sedimentation reaction, and thus the measuring result, is also deleteriously influenced by the shaking and vibrations to which the sample may be subjected during its transportation. The actual transfer of the sample from the vacuum sampling tube to the pipette tube, the so-called dispensing of the sample, also creates with these known methods a considerable risk of spilling some of the blood, which may be contaminated, such spillage being unavoidable in practice. Some of the sample will spill at the moment of withdrawing the stopper from the sampling tube, wherewith part of the sample unavoidably escapes to atmosphere in the form of an aerosol. Although methods and devices have been proposed with which the sampling tube and the pipette tube are coupled together in a manner which enables the sample to be dispensed from the sampling tube to the pipette tube with less risk of spillage, these methods and devices are complicated and relatively time and labour consuming, and also require the provision of additional apparatus.

DISCLOSURE OF THE INVENTION

Accordingly, the object of the present invention is to prvide a device for taking and dispensing a blood sedimentation sample, by means of which the sample can be taken and dispensed without risk of spilling the blood or of the blood escaping, and by means of which the sample can be quickly dispensed in the immediate vicinity of the sampling location in a simple fashion.

The features characterising the device according to the invention are set forth in the following claims.

BRIEF DESCRIPTION OF THE DRAWINGS

The invention will now be described in more detail with reference to a number of embodiments thereof illustrated in the accompanying drawing, in which FIG. 1 is an axially sectioned side view of a first embodiment of the invention together with a conventional sampling holder;

FIG. 2 is an axially sectioned view in larger scale of one end of the device illustrated in FIG. 1;

FIG. 3 is a sectional view taken on the line III—III in FIG. 3; and

FIG. 4 is an axially sectioned side view of a second embodiment of a device according to the invention.

DESCRIPTION OF PREFERRED EMBODIMENTS

FIG. 1 illustrates schematically and by way of example a conventional sampling holder, generally referenced 1, intended for use when taking a sample of blood with the aid of a vacuum sampling tube. The holder 1 includes a cylinder 2, resembling an injection syringe without the plunger, and a double-pointed disposable needle or cannula 3 inserted in one end of the cylinder. The inwardly lying pointed end of the needle 3 is surrounded by a tightly sealing rubber membrane 4, which serves as a mon-return valve.

The device according to the invention illustrated in FIGS. 1-3, and generally referenced 5 includes a sampling tube 6 to which there is firmly connected a pipette tube 7, the pipette tube preferably forming a one-piece structure with the sampling tube 6. The pipette tube 7 has the standard internal diameter and length for determining blood sedimentation, usually 2.5 mm and 200 mm respectively. The open end of the sampling tube 6 is sealed against the ingress of liquid and air by mens of a stopper 8 made of an elastic material, for example rubber, capable of being pierced by a needle or cannula and which will automatically re-seal when the needle is withdrawn. The sampling tube 6 is evacuated, i.e. has an internal partial vacuum, and contains a given amount of anti-coagulant 9, for example a sodium citrate solution. The pipette tube 7 is also evacuated, to create a partial vacuum therein. This evacuation of the tubes 6 and 7 is effected in conjunction with the manufacture of the device.

As will best be seen from FIGS. 2 and 3, the wall of the pipette tube 7, at the end nearest the stopper 8, has provided therein an opening 10. The interior of the pipette tube 7 can be placed in communication with the interior of the sampling tube 6 through the opening 10 and a slit 11 formed in the stopper 8, by rotating the stopper to the position shown in FIGS. 2 and 3. When the stopper occupies this position, the interior of the sampling tube 6 also communicates with the surrounding atmosphere, through a slit 12 in the stopper 8 and a slit 13 in the wall of the sampling tube 6. It will be understood, however, that prior to using the device according to the invention the stopper occupies a position different to that illustrated, for example a position in which the stopper is turned 90° from the illustrated position. Thus, prior to using the device there is no open communication between the interiors of the sampling tube 6 and the pipette tube 7, nor yet between the interior of the sampling tube 6 and atmosphere. In addition, both the interior of the sampling tube 6 and the pipette tube 7 stand under a partial vacuum and the sampling tube contains the aforesaid anti-coagulant 9.

Actual sampling of the blood is effected in a conventional manner by inserting the needle 3 of the sampling holder 1 into a vein of the patient. The device 5 according to the invention is then inserted into the cylinder 2 of the holder 1, so that the inwardly located point of the needle or cannula 3 passes through the stopper 8 and also penetrates the rubber membrane 4 of the sampling holder 1. Blood is then drawn into the sampling tube 6 through the needle 3, under the influence of the partial vacuum prevailing in the sampling tube. When the required amount of blood has been drawn into the sampling tube, this amount being adjusted to the amount of anti-coagulent present, the device 5 according to the invention is withdrawn from the sampling holder 1, whereupon the hole pierced in the stopper 8 by the needle 3 automatically re-seals. The hole pierced in the rubber membrane 4 in the sampling holder 1 also re-seals automatically, so that no blood can be spilled. If the needle is left seated in the view, further samples of blood can be taken in the aforedescribed manner.

The device 5 according to the invention is then shaken from side to side, either manually or preferably in a special cradle designed for this purpose, until the desired mixture of blood and anti-coagulant 9 is obtained. It will be understood that the partial vacuum in the sampling tubes 6 is eliminated, or in any event substantially reduced, as the sample is taken.

The blood sample can then be dispensed immediately, by turning the device 5 according to the invention to a vertical position, with the stopper 8 facing downwards. This can be done to advantage by stopping the cradle used to mix the contents of the tube together with the device 5 in a vertical position. The sample is then dispensed to the pipette tube 7, by turning the stopper 8 to the position illustrated in FIGS. 2 and 3, so that the interior of the sampling tube 6 communicates with the interior of the pipette tube 7 through the slit 11 and the hole 10, and also with the ambient atmosphere through the slits 12 and 13. Under the influence of the partial vacuum prevailing in the pipette tube 7, part of the blood sample will then be drawn automatically into the pipette tube 7 from the sampling tube 6, through the slit 11 and the hole 10, so as to obtain a column of blood of standardised height in the pipette tube 7. At the same time, atmospheric air is able to flow into the sampling tube 6, through the slits 13 and 12. Because the sample is drawn into the pipette tube 7 at the lower end of the pipette tube and from the "bottom" of the sample volume in the sampling tube 6, there is no risk of foam or air bubbles created in the sample during the aforesaid mixing process of accompanying the blood into the pipette tube 7. Air flowing in to the sampling tube 6 through the slits 13 and 12 will bubble up through the sample in the tube 6 without being drawn into the pipette tube 7.

The device is then left in its vertical position for the prescribed period of time for the sedimentation reaction to take place, whereafter the sedimentation rate can be read-off on the pipette tube 7.

In order to prevent blood in the pipette tube 7 from flowing back into the sampling tube 6 during the sedimentation reaction period, the connection formed by the hole 10 and the slit 11 suitably incorporates a non-return valve arrangement. In the illustrated embodiment of the invention, this non-return valve arrangement comprises a plurality of elastic tongues or tabs formed in the slit 11 in the stopper 8, said tongues or tabs permitting the blood to flow solely in one direction, from the sampling tube 6 to the pipette tube 7. It will be understood, however, that the non-return valve arrangement can also have a different form to that illustrated. For example, it may comprise a thin rubber sleeve inserted into the lower part of the pipette tube 7 so as to cover the hole 10.

In order to prevent blood from leaking from the sampling tube 6 to the surrounding, through the slits 12 and 13, a non-return valve arrangement is also suitably provided in this connection. In the illustrated embodiment one such non-return valve arrangement has been provided by giving the slit 12 in the stopper 8 a depth which decreases in a direction towards the interior of the sampling tube 6, so as to form at the end of the slit 12 nearest the interior of the sampling tube 6 an elastic tongue or tab which lies against the inner surface of the wall of said sampling tube 6. Thus, although air is able to flow into the interior of the sampling tube 6 from the surrounding atmosphere through the slits 13 and 12, no blood is able to pass from the interior of the sampling tube 6 through this connection. As will be understood, this non-return valve arrangement may also take other forms.

Subsequent to determining sedimentation in the aforedescribed manner, the whole of the device 5 intended for one-time use only, can be discarded It will be understood that the device according to FIGS. 1–3, can be modified in many ways within the scope of the invention. For example, the openable connections between the respective interiors of the sampling tube 6 and the pipette tube 7 and the surrounding atmosphere respectively can be formed in several different ways. The connection between the interior of the sampling tube 6 and the surrounding atmosphere may be formed, for example, with the aid of a channel in the wall of the sampling tube 6, this channel discharging in the vicinity of the upper end of the sampling tube 6, i.e. the end of the tube opposite the stopper 8, so that the air flowing in from the surrounding atmosphere need never pass through the sample. This entirely eliminates any risk of air bubbles being drawn into the pipette tube 7 by suction. It is also conceivable to arrange the pipette tube 7 relative to the sampling tube 6 in other ways than that illustrated and described, and the pipette tube need not necessarily be integral with the sampling tube but simply firmly connected thereto or provided with means which enables it to be connected to said sampling tube. The arrangement according to the described and illustrated embodiment would seem to be the best arrangement, however.

The embodiment of the device according to the invention illustrated schematically in FIG. 4 differs from the aforedescribed embodiment illustrated in FIGS. 1–3, primarily because no partial vacuum is created in the sampling tube 6 during the manufacture of the device. Instead, the sampling tube 6 is provided with a manually actuable plunger 14. When taking a sample of blood with the aid of a sampling holder 1 (see FIG. 1) in the aforedescribed manner, the requisite partial vacuum can be created within the sampling tube 6 with the aid of this plunger 14. In so doing, the plunger 14 is withdrawn so as to create a partial vacuum within the sampling tube 6, either prior to inserting the sampling tube 6 into the sampling holder 1 or subsequent to having inserted said tube into said holder and subsequent to the rearward pointed end of the needle or cannula 3 having penetrated the rubber stopper 8 of the sampling tube.

Another difference between the FIG. 4 embodiment and the embodiment described with reference to FIGS. 1–3 is that the pipette tube 7 is open at its outer end. In this case, subsequent to mixing the blood sampled in the sampling tube 6 with the anti-coagulant 9 in the aforedescribed manner, the sample is dispensed from the sampling tube to the pipette tube by moving the plunger 14 forwards in the sampling tube 6, so as to force the sample through the connection 10, 11 into the pipette tube 7. Thus, in this embodiment the pipette tube 7 is not under partial vacuum. In order to obtain an accurately determined blood column in the pipette tube 7 and in order to prevent blood from escaping through the open outer end of the pipette tube 7 a freely movable plunger 15 is advantageously arranged in said pipette tube, and the tube is provided at its outer end with a stop means 16 for limiting movement of the plunger 15. It will be understood that this embodiment must incorporate a non-return valve arrangement, for example of the previously described kind, in the connection 10,11 between the pipette tube 7 and the sampling tube 6, so that no air can be drawn into the sampling tube 6 through said connection when the plunger 14 is withdrawn in order to draw a sample of blood into the sampling tube. It will also be understood that the FIG. 4 embodiment requires no connection between the interior of the sampling tube 6 and the surrounding atmosphere. Neither need the stopper 8 be rotated to a new position when dispensing the sample, but that the stopper 8 may constantly occupy a position in which the connection 10, 11 incorporating a non-return valve arrangement prevails between the interiors of the sampling tube 6 and the pipette tube 7.

As will be understood, the embodiment of the invention illustrated in FIG. 4 can be modified so that the pipette tube 7 is closed and stands under a partial vacuum in a manner similar to the embodiment described with reference to FIGS. 1–3, in which case the sample is transferred from the sampling tube 6 to the pipette tube 7 under the influence of this partial vacuum, by opening the connection 10,11. Thus, in this case the stopper 8 must be rotatable, so that the aforesaid connection can be selectively closed and opened. A further conceivable modification in both the embodiment according to FIGS. 1–3 and the embodiment according to FIG. 4 is one in which the pipette tube 7 is open at its outer end and the sample is dispensed from the sampling tube 6 to the pipette tube 7 under the influence of a partial vacuum generated in the pipette tube 7, for example by sucking at the open end of the pipette tube or by means of a withdrawable plunger arranged in the pipette tube. These alternative embodiments, however, are to less advantage than the embodiments described and illustrated with reference to the accompanying drawings.

It will be evident from the aforegoing that a blood sample for determining blood sedimentation can be taken and dispensed by means of a device according to the invention without any risk whatsoever of the blood being spilled. Furthermore, the blood sample can be dispensed quickly and in an extremely simple fashion immediately after taking the sample. This particularly simple and rapid dispensing of the sample affords a particularly important advantage when a plurality of samples are to be dispensed immediately one after the other, so-called series dispensing, with the use of a single time-measurement for all samples taken.

I claim:

1. A device for collecting a blood sample and for determining the blood sedimentation rate of the collected blood sample, comprising:

a sampling tube having one open end; a stopper means inserted in said open end of said sampling tube for sealing said sampling tube against the ingress of air and liquid, said stopper means being made of an elastic self-sealing material capable of being pierced by a hollow needle;

a straight pipette tube having an internal diameter and a length standardized wtih respect to a given method of determining blood sedimentation rate;

said sampling tube and said pipette tube being attached to, and immovable relative to, one another so as to form a single inseparable unit;

a communication passage extending between the interior of said pipette tube and the interior of said sampling tube and being fully sealed against the surroundings;

means for creating a partial vacuum within said sampling tube under the influence of which partial vacuum a blood sample can be drawn into said sampling-tube through a hollow needle adapted to pierce said stopper means; and means for creating a pressure difference between the interior of said sampling tube and the interior for said pipette tube under the influence of which pressure difference a blood sample adapted to be collected to said sampling tube can be transferred to said pipette tube though said communication passage.

2. A device as claimed in claim 1, wherein said sampling tube contains an anti-coagulant.

3. A device for collecting a blood sample and for determining the blood sedimentation rate thereof, comprising:

a sampling tube having one open end;

a stopper means inserted in said open end of said sampling tube for sealing said sampling tube against the ingress of air and liquid, said stopper means being made of an elastic self-sealing material capable of being pierced by a hollow needle;

said sampling tube enclosing a partial vacuum created in conjunction with the manufacture of the device and under the influence of which partial vacuum blood can be drawn into said sampling tube through a hollow needle piercing said stopper means;

a straight pipette tube having an internal diameter and a length standardized with respect to a given method of determining blood sedimentation rate;

said pipette tube being sealed against the surroundings in an air-tight and liquid-tight fashion and including a partial vacuum created in said pipette tube in conjunction with the manufacture of the device;

said sampling tube and said pipette tube being attached to, and immovable relative to, each other so as to form a single inseparable unit;

a first communication passage fully sealed against the surroundings and extending between the interior of said pipette tube and the interior of said sampling tube;

a second communication passage extending between the interior of said sampling tube and the surrounding atmosphere; and manually operable means for selectively closing and opening said first and second communication passages.

4. A device as claimed in claim 3, wherein said sampling tube contains an anti-coagulant.

5. A device as claimed in claim 3, wherein said first communication passage incorporates a non-return valve means for preventing the sample from flowing from said pipette tube to said sampling tube through said first communication passage.

6. A device as claimed in claim 3, wherein said second communication passage incorporates a non-return valve means for preventing the sample from flowing from said sampling tube to the surroundings through said second communication passage.

7. A device as claimed in claim 3, wherein said sampling tube and said pipette tube are disposed parallel to one another side by side with one end of said pipette tube located adjacent said open end of said sampling tube.

8. A device as claimed in claim 7, wherein said first and said second communication passages are formed by recesses in said stopper means and by recesses or openings in walls of said sampling tube and said pipette tube, respectively, and coacting with said recesses in said stopper means.

9. A device as claimed in claim 8, wherein said stopper means is rotatable in said open end of said sampling tube in such a manner that said first and said second communication passages can be selectively opened and closed by rotation of said stopper means to a first position, in which said recesses in said stopper means and in the walls of said sampling tube and said pipette tube, respectively, communicate with one another, and to a second position, in which said recesses in said stopper means and in walls of said sampling tube and said pipette tube, respectively, do not communicate with one another.

10. A device as claimed in claim 8, wherein said stopper means is formed with resilient parts located in said recesses in the stopper means and functioning as non-return valve flaps for preventing the sample from flowing from said pipette tube to said sampling tube through said first communication passage and preventing the sample from flowing from said sampling tube to the surroundings through said second communication passage.

11. A device as claimed in claim 3, wherein said sampling tube and said pipette tube are integral.

12. A device for collecting a blood sample and for determining the blood sedimentation rate thereof, comprising:

a sampling tube having one open end;

a stopper means inserted in said open end of said sampling tube for sealing said sampling tube against the ingress of air and liquid, said stopper means being made of an elastic self-sealing material capable of being pierced by a hollow needle;

a straight pipette tube having an internal diameter and a length standardized with respect to a given method of determining blood sedimentation rate and having a first end closed to the surrounding atmosphere and an opposite second end open to the surrounding atmosphere;

said sampling tube and said pipette tube being attached to, and immovable relative to, one another so as to form a single inseparable unit;

a communication passage fully sealed against the surroundings and extending between the interior of said sampling tube close to said stopper means and the interior of said pipette tube close to said first end, said communication passage incorporating a non-return valve means for preventing air from flowing from the interior of said pipette tube to the interior of said sampling tube through said communication passage; and a manually actuable plunger adapted for axial movement within said sampling tube while sealingly engaging an interior wall surface thereof, whereby said plunger can be withdrawn in said sampling tube for drawing a blood sample into the sampling tube through a hollow needle piercing said stopper means, and said plunger may be subsequently moved forward in the sampling tube for transferring a sample collected in said sampling tube to said pipette tube through said communication passage.

13. A device as claimed in claim 12, wherein said sampling tube contains an anti-coagulant.

14. A device as claimed in claim 12, wherein said communication passage is formed by recesses in said stopper means and by recesses or openings located in walls of said sampling tube and said pipette tube, respectively, and co-acting with said recesses in said stopper means.

15. A device as claimed in claim 14, wherein said non-return valve means comprise resilient parts of said stopper means located in said recesses in the stopper means and functioning as non-return valve flaps.

16. A device as claimed in claim 12, comprising a second plunger freely movable within said pipette tube while sealingly engaging the interior wall surface of said pipette tube, and movement restricting means for said freely movable second plunger arranged in said pipette tube in the vicinity of said second open end of said pipette tube.

17. A device as claimed in claim 12, wherein said sampling tube and said pipette tube are integral.

* * * * *